US007689398B2

(12) United States Patent  
Cheng et al.

(10) Patent No.: US 7,689,398 B2
(45) Date of Patent: Mar. 30, 2010

(54) SYSTEM AND METHOD FOR MODELING AND APPLICATION OF INTERPROXIMAL REDUCTION OF TEETH

(75) Inventors: Jihua Cheng, San Jose, CA (US); Woncheol Choi, San Jose, CA (US); Vadim Matov, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 774 days.

(21) Appl. No.: 11/468,639

(22) Filed: Aug. 30, 2006

(65) Prior Publication Data

US 2008/0057461 A1 Mar. 6, 2008

(51) Int. Cl.
*G06F 9/455* (2006.01)
(52) U.S. Cl. .............................. 703/11; 703/2; 433/24; 700/98
(58) Field of Classification Search ...................... 703/2, 703/11; 433/24, 213, 166, 217.1; 705/3; 700/98
See application file for complete search history.

(56) References Cited

U.S. PATENT DOCUMENTS

| 6,602,070 | B2 * | 8/2003 | Miller et al. ................... 433/24 |
| 6,729,876 | B2 * | 5/2004 | Chishti et al. .................. 433/24 |
| 2002/0064746 | A1 | 5/2002 | Muhammad et al. |
| 2003/0215764 | A1 * | 11/2003 | Kopelman et al. ............. 433/24 |
| 2004/0073417 | A1 * | 4/2004 | Rubbert et al. ................. 703/11 |
| 2004/0197727 | A1 * | 10/2004 | Sachdeva et al. ............... 433/24 |
| 2005/0010450 | A1 * | 1/2005 | Hultgren et al. ................. 705/3 |
| 2005/0058963 | A1 * | 3/2005 | Stockstill ..................... 433/166 |
| 2005/0191594 | A1 * | 9/2005 | Taub et al. ..................... 433/24 |
| 2005/0244791 | A1 * | 11/2005 | Davis et al. ................... 433/213 |
| 2005/0271996 | A1 * | 12/2005 | Sporbert et al. ................ 433/24 |
| 2006/0019218 | A1 * | 1/2006 | Kuo ............................ 433/166 |
| 2006/0068355 | A1 * | 3/2006 | Schultz ......................... 433/24 |
| 2006/0079981 | A1 * | 4/2006 | Rubbert et al. ................. 700/98 |
| 2006/0190301 | A1 * | 8/2006 | Sachdeva ........................ 705/3 |
| 2006/0275736 | A1 * | 12/2006 | Wen et al. ..................... 433/213 |
| 2006/0281041 | A1 * | 12/2006 | Rubbert et al. ................. 433/24 |
| 2007/0003907 | A1 * | 1/2007 | Chishti et al. ............. 433/217.1 |
| 2008/0020350 | A1 * | 1/2008 | Matov et al. .................. 433/213 |

OTHER PUBLICATIONS

Beers et al. "Computer assisted treatment planning and analysis", Orthod Craniofacial Research, vol. 6, 2003.*
Josell et al., "Am overview of Invisalign Treatment", University of Maryland, 2007.*

* cited by examiner

*Primary Examiner*—Paul L Rodriguez
*Assistant Examiner*—Kandasamy Thangavelu
(74) *Attorney, Agent, or Firm*—Klein, O'Neil & Singh, LLP (57) ABSTRACT

In accordance with various aspects of the present invention, system and method for modeling and application of interproximal reduction (IPR) of teeth to facilitate orthodontic treatment is provided. In accordance with an exemplary embodiment, a system and method for modeling and application of IPR are configured within a treatment methodology that initially determines whether stripping is needed for two neighboring teeth. If stripping is necessary, the exemplary method for modeling and application of IPR is conducted. In an exemplary embodiment, a stripping plane or other surface is constructed to determine the amount and region of stripping for two neighboring teeth, in other words, the volume to be removed between two neighboring teeth. After stripping of the tooth, the tooth geometry can be reconstructed to enable application of the IPR tooth model, such as enabling the clinician to utilize the IPR tooth model for teeth movement planning.

45 Claims, 9 Drawing Sheets

FIG. 3A  FIG. 3B Stripping amount

| Stage | 7(31) | 6(30) | 5(29) | 4(28) | 3(27) | 2(26) | 1(25) | 1(24) | 2(23) | 3(22) | 4(21) | 5(20) | 6(19) | 7(18) |
|---|---|---|---|---|---|---|---|---|---|---|---|---|---|---|
| 0 | .00 | .00 | .00 | .00 | .00 | .00 | .00 | .00 | .00 | .00 | .00 | .00 | .00 | |
| 1 | .00 | .00 | .00 | .00 | .00 | .00 | .00 | .08 | .00 | .00 | .00 | .00 | .00 | |
| 2 | .00 | .00 | .00 | .00 | .00 | .00 | .00 | .14 | .00 | .00 | .02 | .00 | .00 | |
| 3 | .00 | .00 | .00 | .00 | .00 | .00 | .00 | .12 | .00 | .00 | .05 | .01 | .00 | |
| 4 | .00 | .00 | .00 | .00 | .00 | .00 | .00 | .08 | .00 | .00 | .07 | .01 | .00 | |
| 5 | .00 | .00 | .00 | .00 | .00 | .00 | .00 | .05 | .00 | .00 | .05 | .00 | .00 | |
| 6 | .00 | .00 | .00 | .00 | .00 | .00 | .00 | .00 | .00 | .00 | .00 | .00 | .00 | |
| 7 | .00 | .00 | .00 | .00 | .00 | .00 | .00 | .00 | .00 | .00 | .00 | .00 | .00 | |
| 8 | | | | | | | | | | | | | | |

Collision after stripping teeth

FIG. 8A

| Stage | 7(31) | 6(30) | 5(29) | 4(28) | 3(27) | 2(26) | 1(25) | 1(24) | 2(23) | 3(22) | 4(21) | 5(20) | 6(19) | 7(18) |
|---|---|---|---|---|---|---|---|---|---|---|---|---|---|---|
| 0 | .00 | .00 | .00 | .00 | .00 | .00 | .00 | .00 | .00 | .00 | .00 | .00 | .00 | |
| 1 | .00 | .00 | .00 | .00 | .02 | .00 | .03 | .08 | .02 | .00 | .00 | .00 | .00 | |
| 2 | .00 | .00 | .00 | .00 | .09 | .05 | .12 | .22 | .08 | .05 | .03 | .01 | .00 | |
| 3 | .00 | .00 | .00 | .00 | .17 | .10 | .20 | .32 | .14 | .10 | .08 | .03 | .00 | |
| 4 | .00 | .00 | .00 | .02 | .23 | .15 | .28 | .40 | .20 | .15 | .12 | .04 | .00 | |
| 5 | .00 | .00 | .00 | .03 | .30 | .20 | .35 | .44 | .27 | .20 | .13 | .05 | .00 | |
| 6 | .00 | .00 | .00 | .04 | .37 | .24 | .43 | .42 | .33 | .25 | .12 | .05 | .00 | |
| 7 | .00 | .00 | .00 | .05 | .43 | .28 | .50 | .39 | .39 | .30 | .10 | .05 | .00 | |
| 8 | | | | | | | | | | | | | | |

Collision without stripping

FIG. 8B

SYSTEM AND METHOD FOR MODELING AND APPLICATION OF INTERPROXIMAL REDUCTION OF TEETH

TECHNICAL FIELD

The present invention relates, generally, to orthodontic treatment, and in particular to a system and method for modeling and application of interproximal reduction of teeth to facilitate orthodontic treatment.

BACKGROUND OF THE INVENTION

One problem experienced during orthodontic treatment is the residual crowding of adjacent teeth due to insufficient interproximal reduction (IPR). The ability to resolve the crowding of teeth to create sufficient space and IPR during treatment is an important issue in the growing field of computational orthodontics. To create such spacing, stripping and/or other trimming processes are most often utilized, but the determination of such stripping and trimming can be very difficult.

For example, clinicians generally do not know in what particular region or area to strip a particular tooth if the stripping is needed. Clinicians generally do not know where the stripping region is located as current quantifying collision functions only output a collision amount. Such processes for determining a stripping region are reactive in nature, rather predicative. Such limitations often mislead the clinician to strip or trim more from a tooth than is necessary, thus resulting in gaps occurring between two neighboring teeth after treatment. Moreover, such limitations may mislead the clinician to strip or trim less from a tooth than is necessary, and/or strip or trim in the wrong region, thus resulting in insufficient space is generated, which hinders tooth to be moved to its target position. In addition, after stripping of the tooth, the stripped IPR tooth geometry cannot be readily visualized in the virtual treatment. Moreover, after such stripping, a clinician cannot be adequately assured whether a stripped or trimmed tooth has sufficient spacing or is still in collision with adjacent teeth, making further adjustment difficult. Since the stripped geometry for the teeth is not adequately represented, the incorrect computation of the collision between teeth during treatment results.

SUMMARY OF THE INVENTION

In accordance with various aspects of the present invention, a system and methods for modeling and application of interproximal reduction (IPR) of teeth to facilitate orthodontic treatment is provided. Such methods for modeling of IPR tooth geometry can comprise generation and construction of the IPR tooth geometry by a modifying the tooth geometry, such as by stripping/trimming or deforming processes, or any other local or applied modification processes of the IPR tooth geometry, such as by extrusion, intrusion, rounding, smoothing and the like. Moreover, such processes can be used alone or suitably combined to generate and construct the modified IPR tooth geometry.

In accordance with an exemplary embodiment, a system and method for modeling and application of IPR are configured within a treatment methodology that initially determines whether stripping is needed for two neighboring teeth. If stripping is necessary, the exemplary method for modeling and application of IPR is conducted, wherein a modified tooth geometry is provided, such as by constructing a stripping plane or other stripping surface to determine the amount and region of trimming for two neighboring teeth, in other words, the volume to be removed between two neighboring teeth. After stripping/trimming of the tooth, the tooth geometry can be reconstructed to enable application of the IPR tooth model, such as enabling the clinician to utilize the IPR tooth model for teeth movement planning. In accordance with another embodiment, rather than using the trimming of the stripping plane or surface, a deformed tooth model can be generated for the IPR tooth geometry by projecting points on the stripping plane or surface.

BRIEF DESCRIPTION OF THE DRAWINGS

The exemplary embodiments of the present invention will be described in connection with the appended drawing figures in which like numerals denote like elements, and wherein.

DETAILED DESCRIPTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for modeling and application of interproximal tooth reduction to facilitate orthodontic treatment as described herein are merely a few of the exemplary applications for the invention. For example, the principles, features and methods discussed may be applied to any orthodontic treatment application.

In accordance with various aspects of the present invention, a system and method for modeling and application of interproximal tooth reduction to facilitate orthodontic treatment are provided. For example, with reference to FIG. 1A, in accordance with an exemplary embodiment, a method for modeling of IPR tooth geometry (104) is configured within a treatment methodology (100) that initially determines in a process whether stripping is needed for two neighboring teeth (102), e.g., at a final stage or position or other interim stages.

Figure 1A:
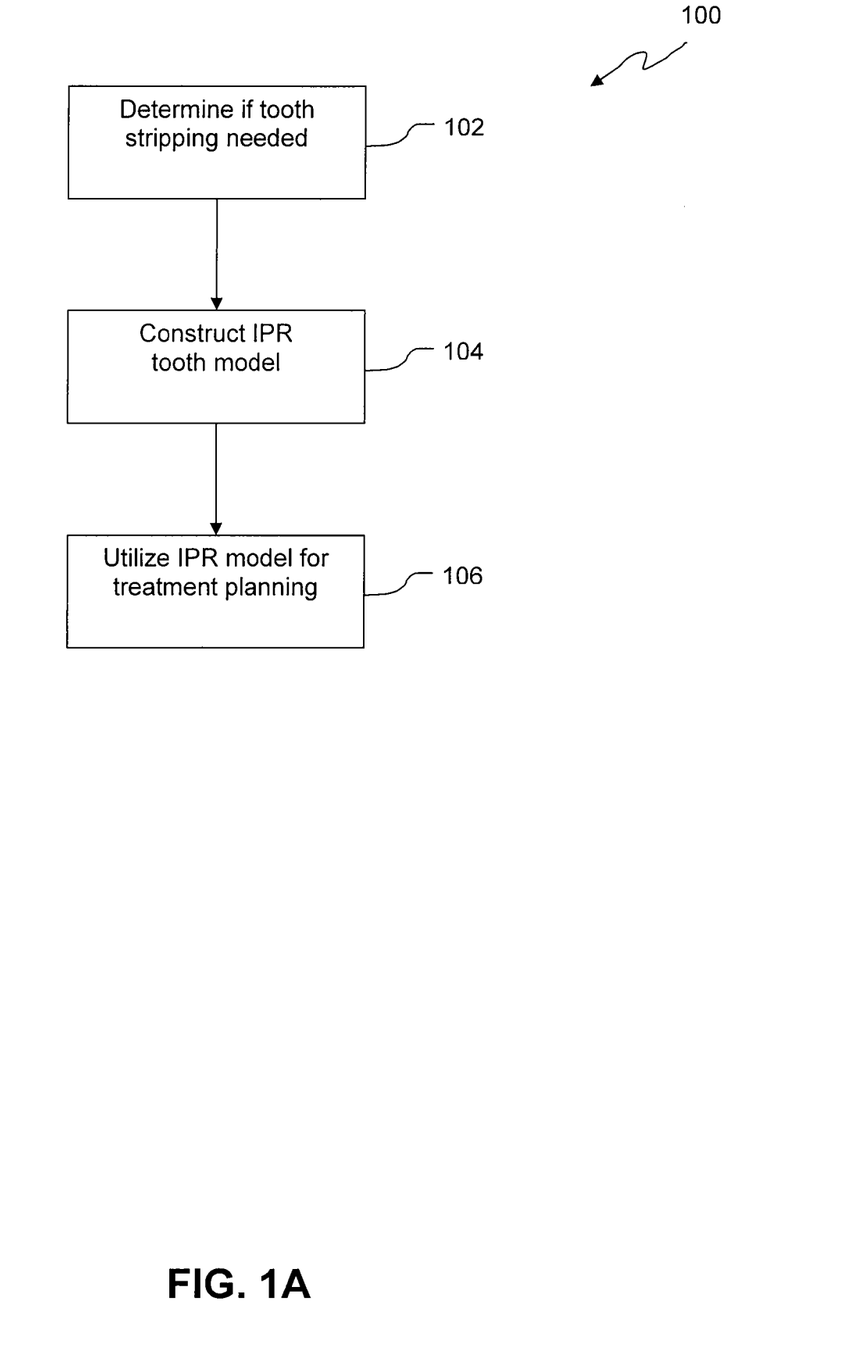
FIGS. 1A and 1B illustrate flow diagrams of an exemplary system and method for treatment comprising constructing of IPR tooth modeling and application in accordance with an exemplary embodiment of the present invention.

If stripping is needed as determined within process (102), method for modeling of IPR (104) comprising the construction and/or calculation of the IPR tooth model or geometry is then conducted. The methods for modeling of (IPR) tooth geometry can comprise generation and construction of a modified IPR tooth geometry by stripping/trimming or deforming processes, or any other local or applied modification processes of the IPR tooth geometry, such as by extrusion, intrusion, rounding, smoothing and the like. Moreover, such processes can be used alone or suitably combined to generate and construct the modified IPR tooth geometry.

In accordance with exemplary embodiment, a stripping surface, such as a stripping plane, is constructed to determine the amount of stripping or trimming for two neighboring teeth, in other words, the volume to be removed between two neighboring teeth. In addition, such a determination can suitably include the specifying of how to conduct the stripping or trimming process, such as the region and amount of stripping for each of the neighboring teeth. It should be noted that the terms "stripping" or "trimming" are used interchangeably when referring to the removal of tooth volume of the IPR tooth geometry.

After stripping of the tooth, the modified tooth geometry can be reconstructed to enable the clinician to visualize the stripped or trimmed geometry, as well as calculate collision/gap at each treatment stage. As a result, the application of the IPR tooth model by the clinician can occur to facilitate teeth movement planning (106).

While the IPR modeling and stripping within treatment methodology (100) may be described and/or illustrated as being based on the final stage or position of teeth, it should be noted that the stripping can be distributed to multiple stages, anywhere from initial stage to final stage. Thus, multiple IPR tooth geometry models can also be generated, wherein such multiple IPR tooth models correspond to any one or all stripping or trimming stages, i.e., multiple, changeable or stage-dependent geometry models can be realized for any or all stripping or trimming stages. Similarly, while the stripping amount calculations described are based on the final stage, wherein the stripping amount comprises the total stripping amount, in other embodiments, the stripping amount can be suitably distributed to one or more stages from initial stage to final stage, with the sum of the multiple stripping amounts comprising the total stripping amount.

Treatment methodology (100) and/or the processes within can be suitably provided from one or more control systems configured for providing the disclosed functions. Such control systems can comprise one or more microprocessors, memory systems and/or input/output devices for processing and/or modeling data and information, and can comprise one or more software algorithms configured for generating complete tooth modeling and/or performing other functions set forth herein.

The determining of whether stripping is needed for two neighboring teeth (102) can be conducted in various maimers through use of an exemplary control system. For example, with additional reference to FIG. 1B, a control system can initiate determining of whether stripping is needed (102) by loading of one or more segmented teeth files (108) into a host computer or other processing system of the control system. Next, the transformation for each tooth at its final stage can be obtained (110) to then apply the transformation to vertices of each tooth (112). The control system can suitably select a particular tooth as the first tooth on the patient's jaw (114) to be checked for stripping requirements, and then determine the neighboring teeth (116) for the first tooth. The control system can then check to see whether overlap with its neighboring teeth exists (118/120), and then proceed to construct the IPR model (104) if overlap for the tooth with its neighboring teeth exists. Although method for determining if stripping is needed for two neighboring teeth (102) can suitably comprise loading of teeth files (108) and getting and applying the transformation to vertices of each tooth to potentially be stripped (110/112), any other methodology, steps or processes for preparing teeth to determine whether overlap exists can be utilized.

Figure 1B:
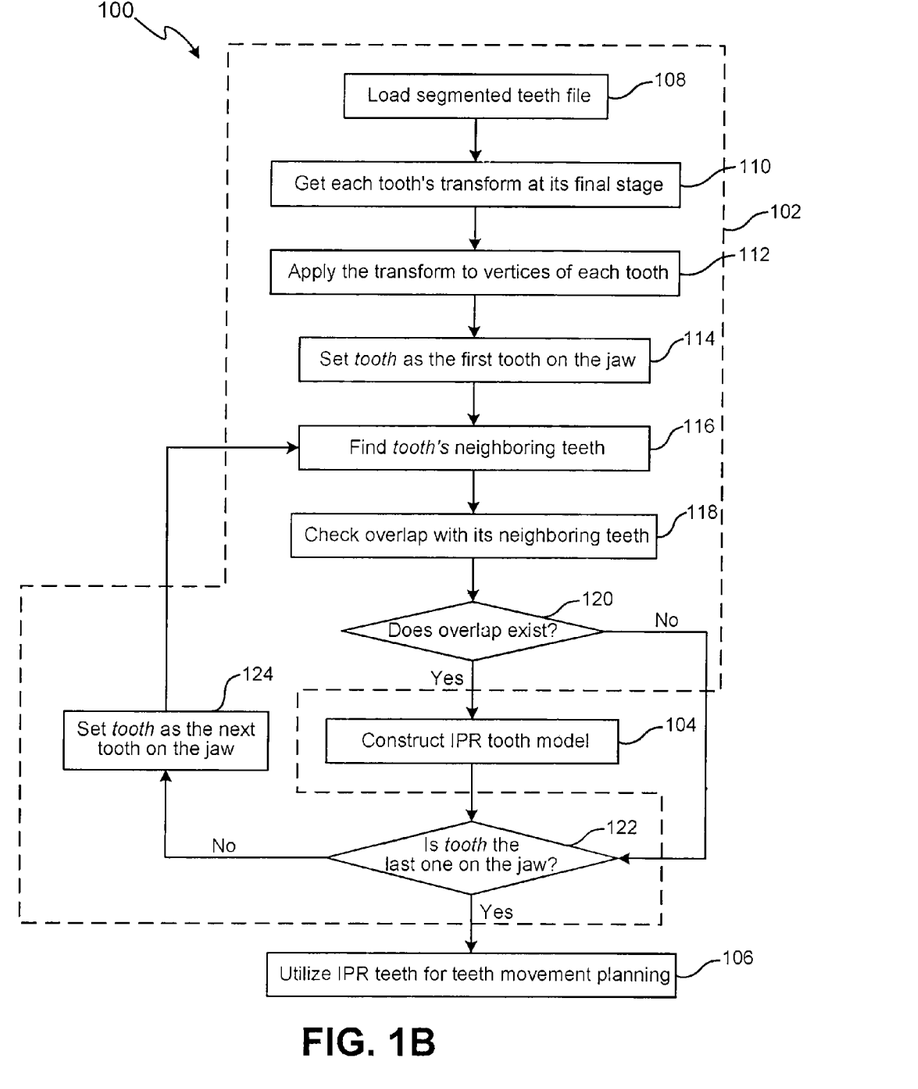

After proceeding to construct the IPR model (104), method 100 can then determine whether to proceed to the next tooth and again determine whether stripping is needed (102), or whether to proceed to teeth movement planning (106) if all teeth have been checked. To determine whether to proceed to the next tooth, treatment method 100 can comprise the steps of determining whether a tooth that has been checked or had an IPR model constructed is the last tooth on the patient's jaw (122), and then if so, proceed to planning (106). If not the last tooth, method 100 can then proceed to the next tooth on the jaw (124) and finding the neighboring teeth (118) for such next tooth. Thereafter, checking of the overlap 118, constructing of IPR tooth model (104) and/or proceeding to determine whether the next tooth is the last one on the patient's jaw (122) can again be conducted before proceeding to teeth movement planning (106).

Figure 2:
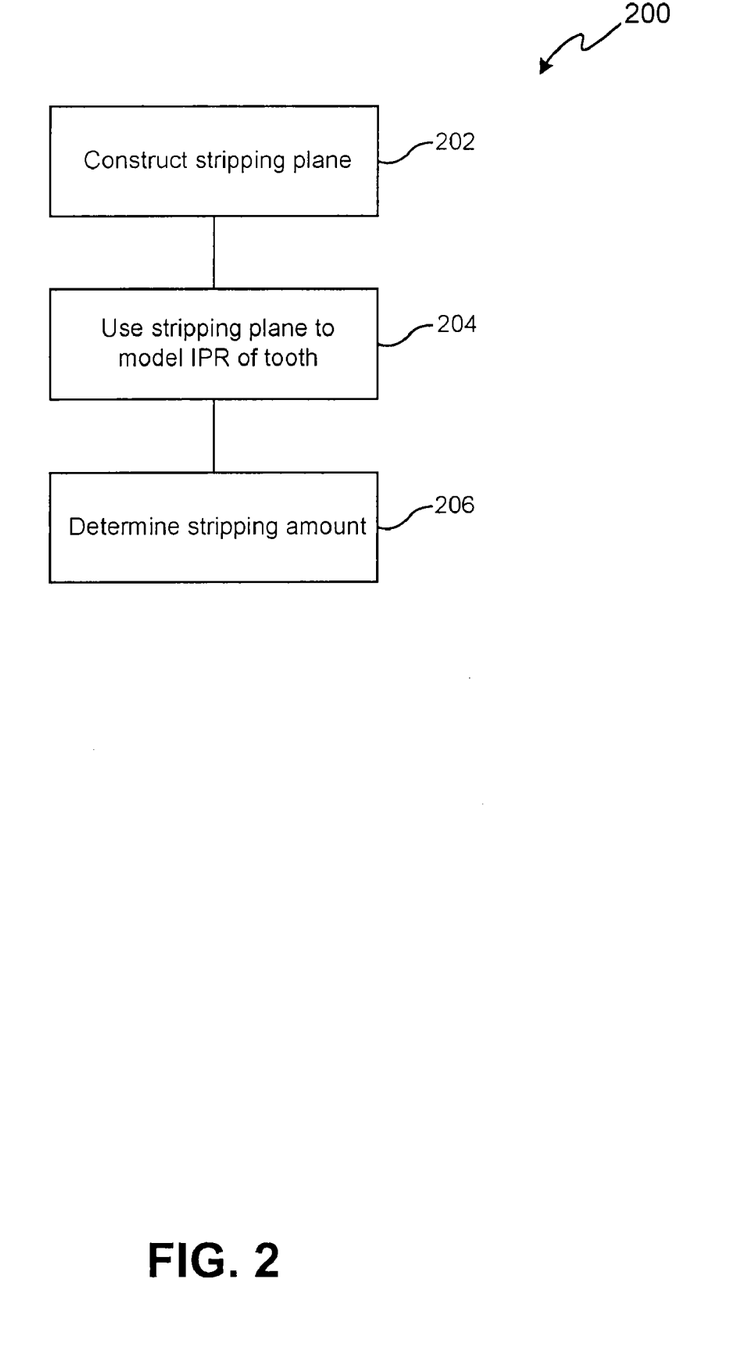
FIG. 2 illustrates a flow diagram of an exemplary method of constructing IPR tooth model in accordance with an exemplary embodiment of the present invention.
Figure 3A:
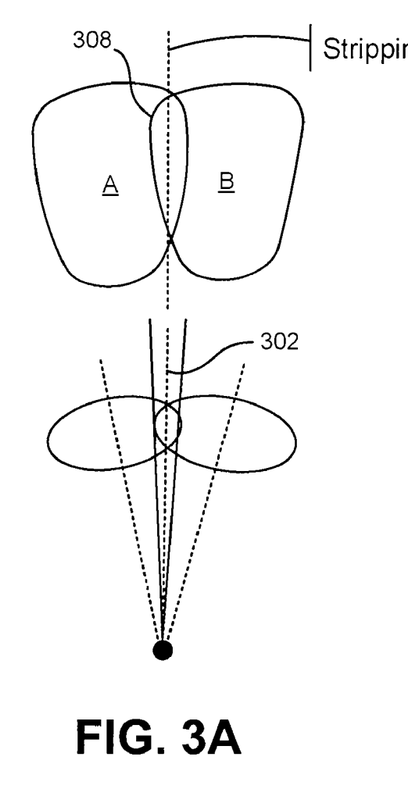
FIGS. 3A and 3B illustrate exemplary graphical representations of a stripping plane and stripping amounts in accordance with exemplary embodiments of the present invention.
Figure 3B:
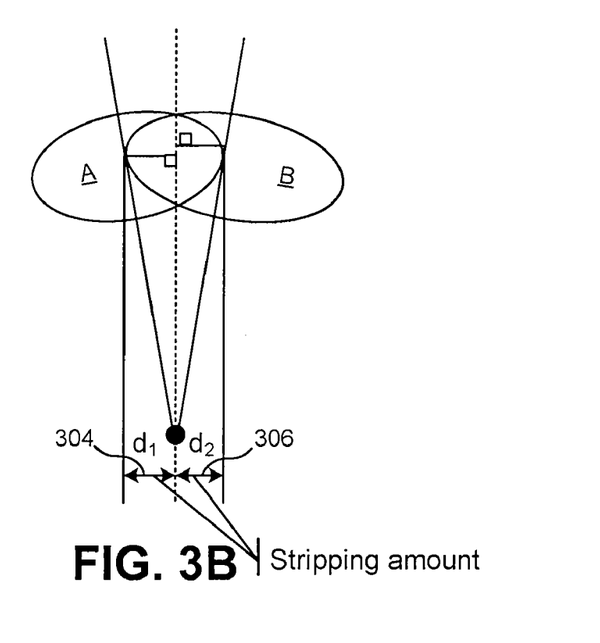

Constructing of the IPR tooth model (104) is suitably configured to specify how to conduct the stripping process, such as the region and amount of stripping or trimming for each of the neighboring teeth. With reference to FIG. 2, in accordance with an exemplary embodiment, a method for constructing of the IPR tooth model 200 comprises the constructing of a stripping plane (202), such as the stripping plane 302 for two neighboring teeth A and B illustrated in FIG. 3A. Using the stripping plane to model the IPR of the tooth (204), method 200 for constructing of the IPR tooth model can then determine the stripping amount (206), such as for example stripping amounts 304 ($d_1$) and 306 ($d_2$) illustrated in FIG. 3B.

In accordance with another exemplary embodiment, rather than the constructing of a stripping surface comprising a stripping plane (202), an exemplary method for constructing of the IPR tooth model 200 can comprise the constructing of another stripping surface configuration, such as a spline surface suitably defined by control points. For example, such a spline surface can be generated by any conventional methodology for providing spline surfaces, such as B-Spline, Bezier, Hermite, Non-Uniform Rational B-Splines (NURBS) or any other appropriate surface, through control points associated with a spline surface. In accordance with other exemplary embodiments, rather than a stripping surface, such as spline surfaces or stripping planes, a method for constructing of the IPR tooth model can comprise the constructing of any other IPR reference for defining an IPR tooth model. Upon generation and constructing of the stripping surface or other IPR references to model the IPR geometry of the tooth (204), method 200 for constructing of the IPR tooth model can then determine the stripping amount (206).

Figure 4:
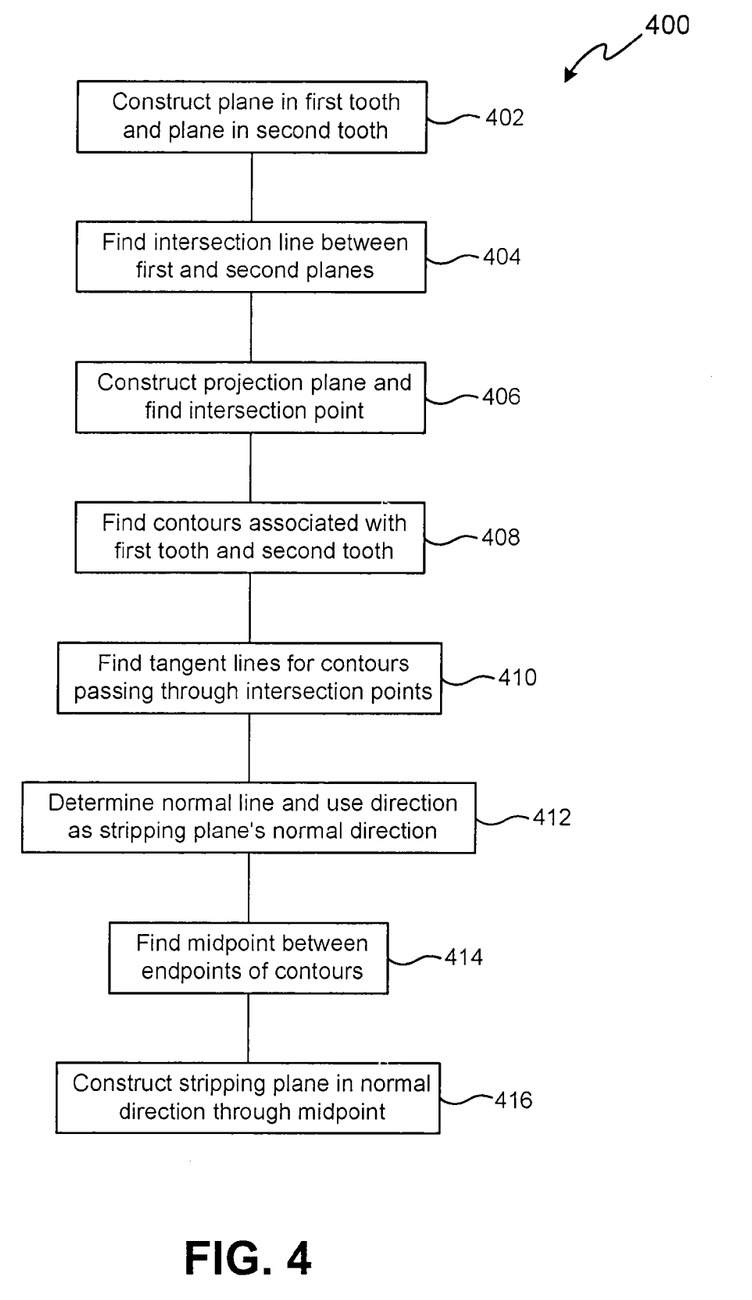
FIG. 4 illustrates a flow diagram of an exemplary method for constructing a stripping plane in accordance with an exemplary embodiment of the present invention.
Figure 5:
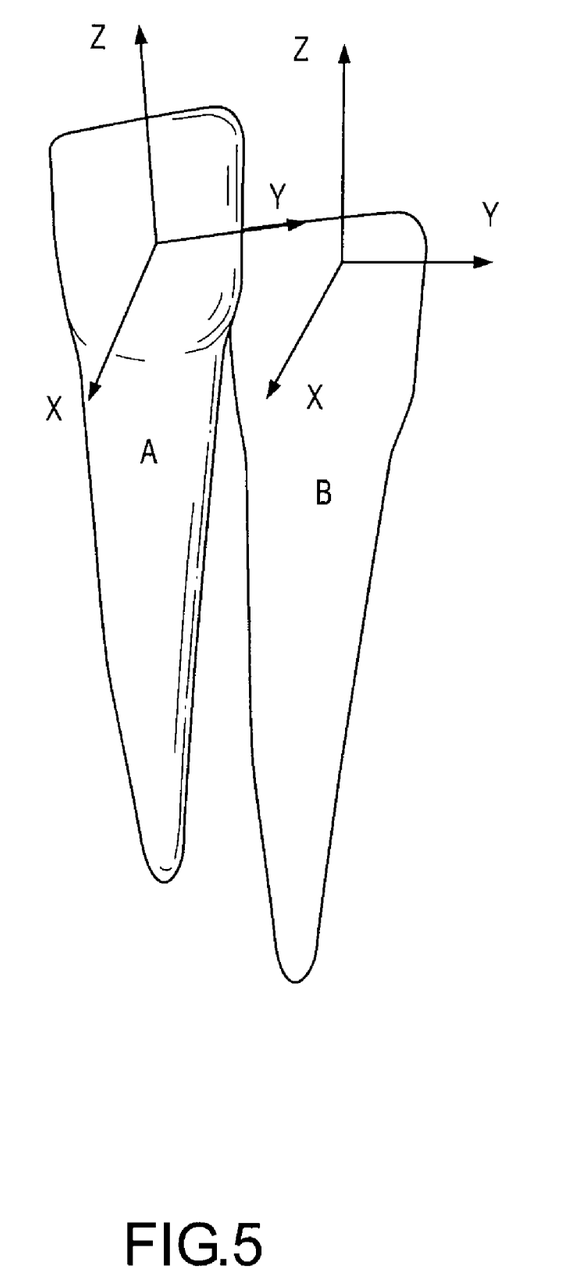
FIG. 5 illustrates an exemplary tooth local coordinate system in accordance with an exemplary embodiment of the present invention.
Figure 6:
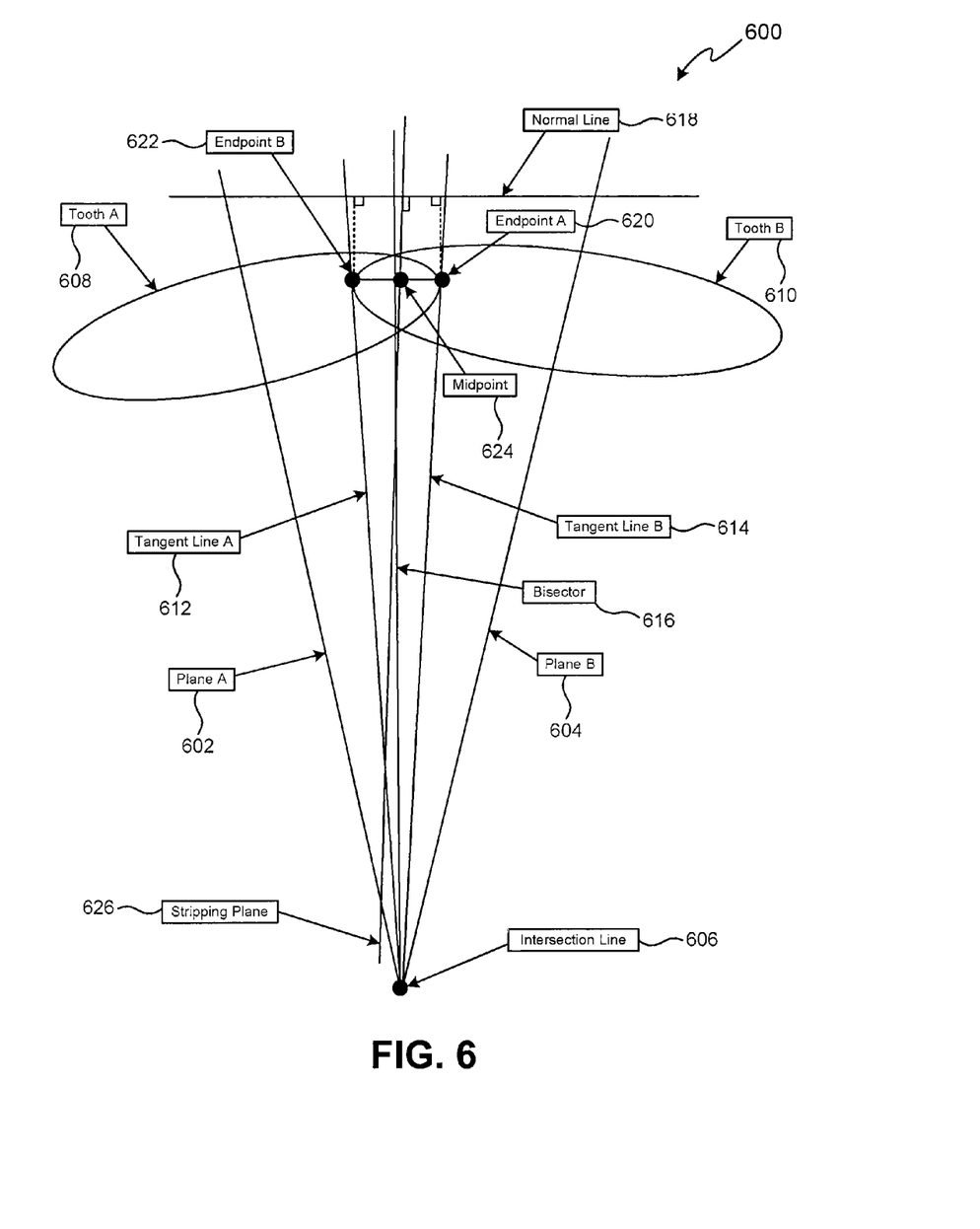
FIG. 6 illustrates a graphical representation for an exemplary view on a projection plane for constructing the stripping plane in accordance with an exemplary embodiment of the present invention.

With reference to FIG. 4, FIG. 5 and FIG. 6, an exemplary method 400 for constructing the stripping plane is illustrated. Such a method is conducted when two neighboring teeth are determined to have overlap, such as neighboring teeth A and B and overlap 308 in FIG. 3A. Method 400 suitably initiates with the constructing a first plane in a first tooth, e.g., tooth A, and a second plane in a second tooth, e.g., tooth B (402). To construct such planes, local coordinate systems or other appropriate references for neighboring teeth A and B are utilized, such as that illustrated in FIG. 5. For example, a plane A is constructed through the origin of the tooth A local coordinate system and whose normal is in the Y-axis direction of the tooth A local coordinate system, while a plane B is constructed through the origin of the tooth B local coordinate system and whose normal is in the Y-axis direction of the tooth B local coordinate system. For example, representative plane A (602) and plane B (604) are illustrated with additional reference to FIG. 6. Instead of local coordinate systems being utilized, other appropriate references such as a facial axis of the clinical crown (FACC) line, an facial-axis (FA) point, a tooth center or any other clinical or geometry feature capable of providing references to facilitate construction of the planes contemplated herein.

Next, method 400 finds the intersection of plane A (602) and plane B (604) that comprises a straight line (404), in other words, finds an intersection line. In accordance with an exemplary embodiment, a projection plane that is perpendicular to the intersection line is then constructed, and then an intersection point between the intersection line and projection plane is determined. For example, with reference to FIG. 6 that comprises a view of the projection plane, intersection line (606) appears as a single point when viewed on the projection plane, with the intersection of line (606) and the projection plane defining the intersection point.

While the projection plane can be suitably constructed by constructing planes A and B (402), finding the intersection line (404) and constructing the projection plane perpendicular to the intersection line, the projection plane can be suitably constructed in various other manners in accordance with other exemplary embodiments. For example, in accordance with another exemplary embodiment, the normal of the projection plane can be determined through the equation:

Normal vector of Projection Plane=$W_A*NZ_A+W_B*NZ_B$ where $NZ_A$ is the unit vector of the Z-axis of the local coordinate system for tooth A and $NZ_B$ is the unit vector of the Z-axis of the local coordinate system for tooth B, allowing construction of the projection plane, and $W_A$ and $W_B$ are the weight coefficients of $NZ_A$ and $NZ_A$ with $W_A \geq 0$, $W_B \geq 0$ and $W_A+W_B=1$. For example, weight coefficients $W_A$ and $W_B$ can each comprise ½, e.g., for equal weighting and thus impact of weight coefficients $W_A$ and $W_B$, or any other suitable ratio ($W_A:W_B$). For example, when $NZ_A$ direction is more preferred by a clinician, the ratio is greater than 1, i.e. $W_A>W_B$. When $NZ_B$ direction is more preferred by a clinician, the ratio is less than 1, i.e. $W_A<W_B$. If neither of them is preferred, the ratio can simply selected as 1, i.e. $W_A=W_B=0.5$. In accordance with another exemplary embodiment, the normal of the projection plane can also be determined through the equation:

Normal vector of Projection Plane=$\Sigma W_i*NZ_i$ where $NZ_i$ is the unit vector of the Z-axis of the local coordinate system for tooth i and n is the total tooth number on the patient's jaw and Wi is the weight coefficient of NZi with $Wi \geq 0$, and $\Sigma Wi=1$. If no preference of $NZ_i$'s direction exists, each $W_i$ can simply selected equally as i/n. When the direction of $NZ_i$ is more preferred, its corresponding $W_i$ is greater than i/n. When certain $NZ_i$'s direction is less preferred, its corresponding $W_i$ is less than i/n.

In accordance with yet another exemplary embodiment, the arch form curve can be used to construct the projection plane. An arch form curve is a smooth curve that is an approximation of all facial axis (FA) points on a patient's jaw. Ideally, an arch form curve comprises the optimal position of FA points after treatment. For example, in an exemplary embodiment, the arch form curve is created by the FA points at final stage. On the arch form curve, an intermediate point between an FA point on Tooth A and an FA point on Tooth B is found to construct an osculating plane, which is used as the projection plane. In accordance with yet another exemplary embodiment, the occlusal plane can be used as the projection plane. The occlusal plane is constructed for the lower arch. For well aligned teeth, the occlusal plane is the plane which passes through the tips of the front incisors and highest points of the first molars in such a way that all teeth points (except the points of canines) are below the plane. In an exemplary embodiment, the occlusal plane is the plane which best approximates the mentioned four points.

After finding the intersection point (406), contours associated with the first tooth A and the second tooth B are determined (408). In this process, all the vertices of the crown surface of Tooth A are projected on the projection plane, with the contour of the projection points comprising contour A, e.g., a contour 608 illustrated in FIG. 6, and all the vertices of the crown surface of tooth B are projected on the projection plane, with the contour of the projection points comprising contour B, e.g., a contour 610 illustrated in FIG. 6. Next, a tangent line for contour A (608) and a tangent line for contour B (610) that go through the intersection point are found (410). For example, a tangent line A (612) and a tangent line B (614) that pass through intersection point 606 in FIG. 6 can be determined.

Next, a normal line is constructed, whose direction determines the normal direction for the stripping plane (412). In accordance with an exemplary embodiment, with additional reference to FIG. 6, a bisector 616 is calculated from the intersection angle formed by tangent line A (612) and tangent line B (614). A normal line 618 is constructed that lies in the projection plane and is perpendicular to bisector 616. Normal line 618 can also be constructed in other manners. For example, in accordance with an exemplary embodiment, the direction vector of normal line 618 can be determined through the equation:

Direction Vector of Normal Line=$W_A*NY_A+W_B*NY_B$ where $NY_A$ is the unit vector of the Y-axis of the local coordinate system for tooth A and $NY_B$ is the unit vector of the Y-axis of the local coordinate system for tooth B, and $W_A$ and $W_B$ are the weight coefficients of $NY_A$ and $NY_B$ with $W_A \geq 0$, $W_B \geq 0$ and $W_A+W_B=1$. For example, weight coefficients $W_A$ and $W_B$ can each comprise ½, e.g., for equal weighting and thus impact of weight coefficients $W_A$ and $W_B$, or any other suitable ratio ($W_A:W_B$). When $NY_A$'s direction is more preferred, the ratio is greater than 1, i.e. $W_A>W_B$. When $NY_B$'s direction is more preferred, the ratio is less than 1, i.e. $W_A<W_B$. If neither of them is preferred, the ratio can simply selected as 1, i.e. $W_A=W_B=0.5$. In accordance with yet another exemplary embodiment, the arch form curve can be used to construct the normal line 618 and direction. On the arch form curve, an intermediate point between an FA point of Tooth A and an FA point on Tooth B is found and the tangent vector at this intermediate point is used as the direction vector of normal line 618. Regardless of the methodology used to construct normal line 618, the direction of normal line 618 comprises the normal direction of the stripping plane.

In accordance with an exemplary embodiment, an intermediate point that comprises a midpoint between the endpoints of contours of tooth A (608) and tooth B (610) is then determined (414). For example, the rightmost point of contour A (608) in the normal direction is determined as a first endpoint A (620), and the leftmost point of contour B (610) in the normal direction is determined as a second endpoint B (622). A midpoint 624 of the line segment between endpoints A (620) and B (622) can then be found. Having identified midpoint 624, a stripping plane 626 can be suitably constructed (416) that goes through midpoint 624 and whose normal direction comprises the direction of normal line 618.

Such use of midpoint 624 is suited when two neighboring teeth A and B are to be stripped equally, i.e., wherein the ratio of stripping for teeth A and B is a 1:1 ratio. However, in accordance with other exemplary embodiments, when different amounts of stripping are to be conducted for two neighboring teeth A and B, another intermediate point between endpoint A (620) and endpoint B (622) can be suitably utilized. For example, when different amounts of stripping are needed, the normal of stripping plane 626 can first be determined. Next, different amounts of stripping for two neighboring teeth A and B can then be determined automatically, such as by calculating the ratio based on the size or volume for two neighboring teeth A and B, or interactively, such as by allowing a clinician to access a user interface and manually specify the ratio of the two stripping amounts. Then the stripping plane can be determined by normal line 618 and the intermediate point as determined by the selected ratio of the two stripping amounts of Tooth A and Tooth B.

With reference again to FIG. 2, having constructed a stripping plane (202), the stripping plane can then be used to model the IPR (204). For example, in accordance with an exemplary embodiment, with additional reference to FIG. 7, a left stripping plane 702 and a right stripping plane 704 can be used to trim the tooth three-dimensional model, with the trimmed tooth model being used as the IPR tooth model for further treatment planning. In accordance with other exemplary embodiments, rather than using the stripping plane to facilitate trimming of the three-dimensional IPR tooth geometry, another type of stripping surface can be utilized, such as spline surface.

Figure 7:
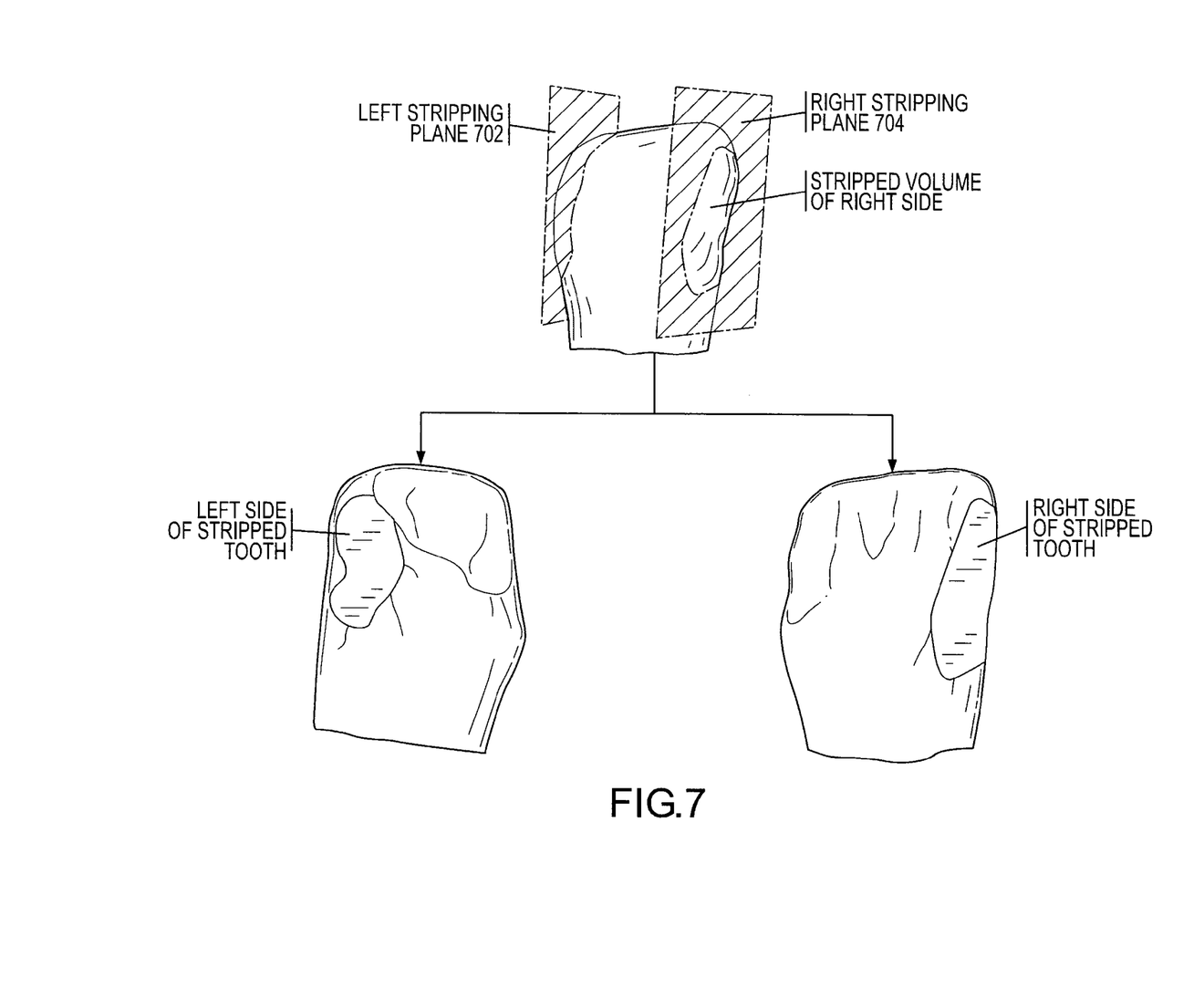
FIG. 7 illustrates exemplary graphical visualizations of left and right stripping planes in accordance with an exemplary embodiment of the present invention.

In accordance with another exemplary embodiment, rather than using a trimmed tooth model to obtain the modified IPR tooth geometry, an exemplary method can use a deformed tooth model to provide the IPR tooth model. For example, the geometry of the vertices that are located on the left of left stripping plane 702 or the right of right stripping plane 704 can be adjusted by projecting all of the points on the left of the left stripping plane onto left stripping plane 702, and all of the points on the right of the right stripping plane onto right stripping plane 704, with such a change in coordinates of the vertices resulting in a deformed tooth model that can then be used as the IPR tooth model. In accordance with other exemplary embodiments, rather than projecting all such points onto the left or right stripping planes 702 and 704, such projecting of points can be provided onto other stripping surfaces, such as spline surfaces and the like. Such a deformed tooth model can provide another optional implementation of IPR tooth modeling that may be simpler or easier as compared with the various other exemplary methods. Moreover, other local or applied modification processes of the IPR tooth geometry, such as by extrusion, intrusion, rounding, smoothing and the like can also be suitably utilized, alone or in combination with the stripping/trimming and/or deformed tooth modeling processes based on the potential for collision between any neighboring teeth.

Based on the developed IPR tooth models, the amount of stripping can then be determined (206) as the amount of stripping can be both quantified and visualized. For example, the amount of stripping can be represented by the distance from the leftmost/rightmost point of a stripped tooth model to the stripping plane or stripping surface. Also the amount of stripping can be represented by the trimmed volume. Thus, for example, the trimmed or deformed IPR tooth model can comprise the 3D digital model which can be visualized in the computer system.

After a tooth has been stripped to avoid collision, the geometry of the tooth will be changed, as well as the approximate relationship between that tooth and any neighboring teeth. When such stripping occurs, there are various possible outcomes for the teeth resulting from stripping based on the IPR model, such as the development of a gap between the neighboring teeth, a reduction in the collision, and/or the teeth still contacting each other. Such post-stripping approximation information gathered from the IPR tooth model can be provided in a collision/gap report to the treatment provider to facilitate further stage planning, rescheduling and/or adjustments to treatment plans.

Figure 8A:
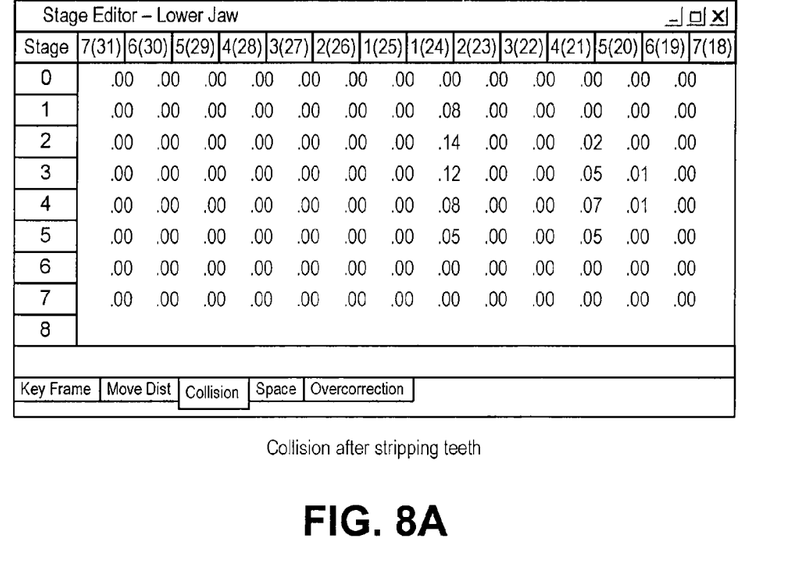
FIGS. 8A and 8B illustrate exemplary collision reports in accordance with exemplary embodiments of the present invention.
Figure 8B:
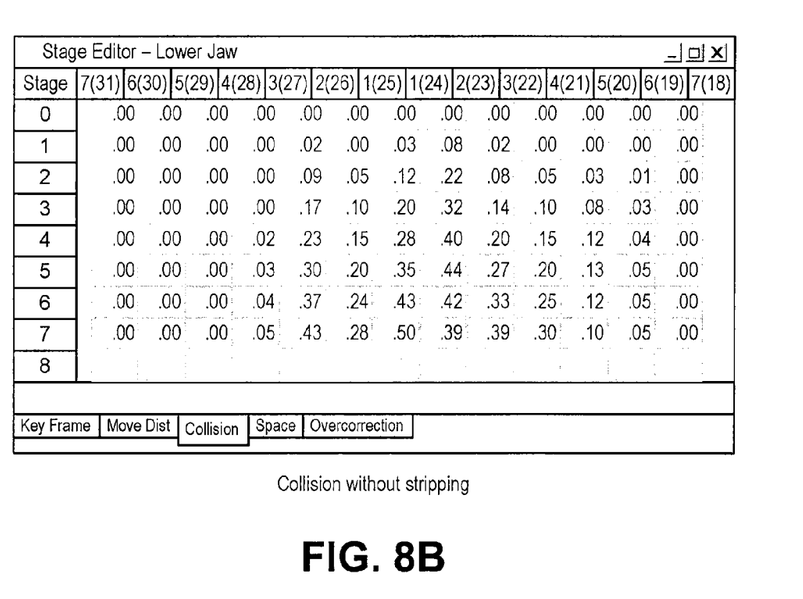

For example, with reference to FIGS. 8A (post-stripping) and 8B (pre-stripping), exemplary collision/gap reports can suitably identify the amount of collision and/or gap between teeth at various stages of treatment. Thus, for example, while the amount of collision between teeth 1(25) and 1(24) slowly increases through stage 7 and can comprise 0.50 mm in a pre-stripping model at stage 7, after stripping through the IPR tooth model, the collision is eliminated between those neighboring teeth 1(25) and 1(24) throughout the staging process. Meanwhile, the amount of collision between teeth 1(24) and 2(23) increases through stage 7 to approximately 0.39 mm in a pre-stripping model, after stripping with the IPR tooth model, the collision between those neighboring teeth 1(24) and 2(23) is substantially reduced in stages 1 through 5 with some minimal collision amounts, and eliminated in stages 6 and 7. Through such a collision/gap report, further stage planning, rescheduling and/or adjustments can be set forth by the treatment provider to facilitate improved treatment, using the collision/gap reports as a useful reference.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the component and methodologies and/or steps may be deleted, modified, or combined with other components, methodologies and/or steps. For example, various of the methods, systems and devices, such as utilizing tooth local coordinate system, constructing the normal vector of projection plane, and deforming tooth geometry, can suitably utilize any other conventional techniques, or any later developed techniques. Further, it should be noted that the method and system for constructing the stripping plane, defining/quantifying stripping amount, modeling IPR tooth, and/or utilizing IPR tooth model can be adjusted or modified. These and other changes or modifications are intended to be included within the scope of the present invention, as set forth in the following claims.

The invention claimed is:

1. A computerized system for interproximal reduction (IPR) tooth modeling of a patient to facilitate orthodontic treatment, said computerized system comprising:
   a microprocessor; and a memory device including instructions for a plurality of algorithms;

wherein the microprocessor is configured for:

determining whether a tooth has a potential for overlap with at least one neighboring tooth;

generating a three-dimensional IPR tooth model for the tooth based on the potential for overlap between the tooth and at least one neighboring tooth including constructing a stripping surface for the tooth by constructing a stripping plane for the tooth by determining a normal direction of the stripping plane based on local coordinate systems for the tooth or other appropriate references and the at least one neighboring tooth, and determining a target point between contours associated with the tooth and the at least one neighboring tooth, with the stripping plane being constructed to pass through the target point and in the normal direction; and developing an orthodontic treatment plan to facilitate the movement of the tooth and the at least one neighboring tooth from an initial position to a final position using the three-dimensional IPR tooth model.

2. The computerized system according to claim 1, wherein the microprocessor is further configured for determining a stripping amount for said tooth.

3. The computerized system according to claim 1, wherein said generating an IPR tooth model for said tooth utilizes a modified IPR tooth geometry to represent said IPR tooth model.

4. The computerized system according to claim 1, wherein said generating an IPR tooth model for said tooth comprises utilizing at least one of a trimmed tooth and a deformed tooth to represent said IPR tooth model.

5. The computerized system according to claim 1, wherein said constructing a stripping surface for said tooth comprises constructing a spline surface.

6. The computerized system according to claim 1, wherein said constructing a stripping surface for said tooth is used to construct at least one of a trimmed IPR tooth model and a deformed IPR tooth model.

7. The computerized system according to claim 1, wherein the microprocessor is configured for determining the normal direction of said stripping plane by constructing a normal line having a direction vector defined by the equation:

Direction Vector of Normal Line=$W_A*NY_A+W_B*NY_B$ wherein $NY_A$ is a unit vector of a Y-axis of a local coordinate system for said tooth and $NY_B$ is a unit vector of a Y-axis of a local coordinate system for said at least one neighboring tooth, and $W_A$ and $W_B$ are the weight coefficients of $NY_A$ and $NY_B$ with $W_A>0$, $W_B>0$ and $W_A+W_B=1$.

8. The computerized system according to claim 1, wherein the microprocessor is configured for determining the normal direction of said stripping plane by using an arch form curve.

9. The computerized system according to claim 1, wherein the microprocessor is configured for determining the normal direction of said stripping plane by constructing a normal line that lies within a projection plane and is perpendicular to a bisector, said bisector calculated based on an intersection angle formed by a first tangent line associated with said tooth and a second tangent line associated with said at least one neighboring tooth.

10. The computerized system according to claim 9, wherein said projection plane is defined by the equation:

Normal of Projection Plane=$W_A*NZ_A+W_B*NZ_B$ where $NZ_A$ is a unit vector of a Z-axis of the local coordinate system for said tooth and $NZ_B$ is a unit vector of a Z-axis of the local coordinate system for said at least one neighboring tooth, and $W_A$ and $W_B$ are the weight coefficients of $NZ_A$ and $NZ_B$ with $W_A>0$, $W_B>0$ and $W_A+W_B=1$.

11. The computerized system according to claim 9, wherein said projection plane is defined by the equation:

Normal of Projection Plane=$\Sigma W_i*NZ_i$ where $NZ_i$ is a unit vector of the Z-axis of the local coordinate system for a tooth i and n represents a total tooth number for the patient and $W_i$ is the weight coefficient of $NZ_i$ with $W_i->0$, and $\Sigma W_i=1$.

12. The computerized system according to claim 9, wherein said projection plane is constructed by:

constructing a first plane in said tooth through an origin of a local coordinate system for said tooth, with a normal for said first plane in a Y-axis direction of said local coordinate system for said tooth;

constructing a second plane in at least one neighboring tooth of said tooth through an origin of a local coordinate system for said at least one neighboring tooth, with a normal for said second plane in a Y-axis direction of said local coordinate system for said neighboring tooth; and finding an intersection line between said first plane and said second plane, wherein said projection plane is constructed perpendicular to said intersection line.

13. The computerized system according to claim 12, wherein said first tangent line and said second tangent line are constructed by:

finding an intersection point defined between said intersection line and said projection plane, said project plane being perpendicular to said intersection line;

projecting vertices on a crown surface of said tooth to define a contour of said tooth;

projecting vertices on a crown surface of said at least one neighboring tooth to define a contour of said at least one neighboring tooth; and constructing said first tangent line through said intersection point and tangent to said contour of said tooth; and constructing said second tangent line through said intersection point and tangent to said contour of said at least one neighboring tooth.

14. The computerized system according to claim 13, wherein said target point comprises a midpoint or an intermediate point configured between endpoints associated with said contour of said tooth and said contour of said at least one neighboring tooth.

15. A computerized method for interproximal reduction (IPR) tooth modeling of a patient to facilitate orthodontic treatment, said computerized method for IPR tooth modeling comprising:

determining, using a computer, whether a first tooth has a potential for overlap with any neighboring teeth;

generating, using the computer, an IPR tooth model for the first tooth based on the potential for overlap with any neighboring teeth including constructing a stripping surface for the first tooth by constructing a stripping plane for the first tooth by determining a normal direction of the plane based on local coordinate systems for the first tooth or other appropriate references and any neighboring teeth, and determining a target point between contours associated with the first tooth and the neighboring teeth, with the stripping plane being constructed to pass through the target point and in the normal direction; and developing, using the computer, an orthodontic treatment plan to facilitate the movement of the first tooth and the neighboring teeth from an initial position to a final position using the IPR tooth model, and wherein the using the IPR tooth model includes computer visualization of the IPR tooth model.

16. The computerized method according to claim 15, wherein said generating an IPR tooth model for said tooth utilizes a trimmed tooth to represent said IPR tooth model.

17. The computerized method according to claim 15, wherein said generating an IPR tooth model for said tooth utilizes a deformed tooth to represent said IPR tooth model.

18. The computerized method according to claim 15, wherein said constructing a stripping surface for said tooth comprises constructing a spline surface.

19. The computerized method according to claim 15, wherein said stripping surface for said tooth is used to construct at least one of a trimmed IPR tooth model and a deformed IPR tooth model.

20. The computerized method according to claim 15, wherein said determining a normal direction of said stripping plane comprises defining said normal line by the equation:

$$\text{Direction Vector of Normal Line} = W_A * NY_A + W_B * NY_B$$

wherein $NY_A$ is a unit vector of a Y-axis of a local coordinate system for said tooth and $NY_B$ is a unit vector of a Y-axis of a local coordinate system for said at least one neighboring tooth, and $W_A$ and $W_B$ are the weight coefficients of $NY_A$ and $NY_B$ with $W_A > 0$, $W_B > 0$ and $W_A + W_B = 1$.

21. The computerized method according to claim 15, wherein said determining a normal direction of said stripping plane comprises defining said normal line by using an arch form curve.

22. The computerized method according to claim 15, wherein said determining a normal direction of said stripping plane comprises constructing a normal line that lies within a projection plane and is perpendicular to a bisector, said bisector calculated based on an intersection angle formed by a first tangent line associated with said tooth and a second tangent line associated with said at least one neighboring tooth.

23. The computerized method according to claim 22, wherein said projection plane is defined by the equation:

$$\text{Normal of Projection Plane} = W_A * NZ_A + W_B * NZ_B$$

where $NZ_A$ is a unit vector of a Z-axis of the local coordinate system for said tooth and $NZ_B$ is a unit vector of a Z-axis of the local coordinate system for said at least one neighboring tooth, and $W_A$ and $W_B$ are the weight coefficients of $NZ_A$ and $NZ_B$ with $W_A > 0$, $W_B > 0$ and $W_A + W_B = 1$.

24. The computerized method according to claim 22, wherein said projection plane is defined by the equation:

$$\text{Normal of Projection Plane} = \Sigma W_i * NZ_i$$

where $NZ_i$ is a unit vector of the Z-axis of the local coordinate system for a tooth i and n represents a total tooth number for the patient and $W_i$ is the weight coefficient of $NZ_i$ with $W_i > 0$, and $\Sigma W_i = 1$.

25. The computerized method according to claim 22, wherein said projection plane is constructed by:
constructing a first plane in said tooth through an origin of a local coordinate system for said tooth, with a normal for said first plane in a Y-axis direction of said local coordinate system for said tooth;
constructing a second plane in at least one neighboring tooth of said tooth through an origin of a local coordinate system for said neighboring tooth, with a normal for said second plane in a Y-axis direction of said local coordinate system for said neighboring tooth; and
finding an intersection line between said first plane and said second plane.

26. The computerized method according to claim 15, wherein said stripping plane is used to generate said IPR tooth model by trimming a three-dimensional model of a tooth.

27. The computerized method according to claim 15, wherein said stripping plane is used to generate said IPR tooth model by generating a deformed tooth model.

28. The computerized method according to claim 27, wherein said deformed tooth model is generated by adjusting geometry of vertices located on one side of said stripping plane.

29. The computerized method according to claim 28, wherein said generating a deformed tooth model by adjusting geometry of vertices located on one side of the stripping plane comprises projecting all points located on said one side of said stripping plane onto said stripping plane.

30. The computerized method according to claim 15, wherein said computerized method further comprises determining a stripping amount of said first tooth and at least one neighboring tooth.

31. The computerized method according to claim 30, wherein said determining a stripping amount of said first tooth and at least one neighboring tooth comprises computer visualization of said stripping amount.

32. The computerized method according to claim 31, wherein said determining a stripping amount of said first tooth and at least one neighboring tooth comprises generating a three-dimensional representation illustrating a removed portion from the first tooth and at least one neighboring tooth equivalent to the stripping amount.

33. A computerized method for facilitating orthodontic treatment planning, said computerized method comprising:
determining, using a computing device, whether stripping is needed for a tooth between any neighboring teeth based on potential collision with the neighboring teeth;
generating, using the computing device, an interproximal reduction (IPR) tooth model for said tooth based on the potential collision with the neighboring teeth including constructing a stripping surface for the tooth by constructing a stripping plane for the tooth by determining a normal direction of the stripping plane based on local coordinate systems for the tooth or other appropriate references and at least one neighboring tooth, and determining a target point between contours associated with the tooth and the at least one neighboring tooth, with the stripping plane being constructed to pass through the target point and in the normal direction; and
determining, using the computing device, a stripping amount for said tooth using the IPR tooth model.

34. The computerized method according to claim 33, wherein said stripping surface is used to construct one of a trimmed IPR tooth model and a deformed IPR tooth model.

35. The computerized method according to claim 33, wherein said stripping plane is used to generate said IPR tooth model by trimming a three-dimensional model of a tooth.

36. The computerized method according to claim 33, wherein said stripping plane is used to generate said IPR tooth model by generating a deformed tooth model by adjusting geometry of vertices located on one side of the stripping plane.

37. The computerized method according to claim 33, wherein said determining a stripping amount of said tooth comprises generating a three-dimensional representation illustrating a stripped portion from said tooth equivalent to the stripping amount to provide a computer visualization of the stripped tooth.

38. A computerized method for modeling and application of interproximal reduction for a tooth comprising:
   determining, using a computer, whether stripping is needed for a tooth between any neighboring teeth based on potential collision with the neighboring teeth;
   generating, using the computer, an interproximal reduction (IPR) tooth model for said tooth by constructing a modified tooth geometry based on the potential collision with the neighboring teeth including constructing a stripping surface for the tooth by constructing a stripping plane for the tooth by determining a normal direction of the stripping plane based on local coordinate systems for the tooth or other appropriate references and at least one neighboring tooth, and determining a target point between contours associated with the tooth and the at least one neighboring tooth, with the stripping plane being constructed to pass through the target point and in the normal direction; and
   determining, using the computer, a stripping amount for said tooth, including generating a three-dimensional representation illustrating a stripped portion from the tooth equivalent to the stripping amount to provide a computer visualization of the stripped tooth.

39. The computerized method according to claim 38, wherein said generating an IPR tooth model for said tooth comprises using an IPR reference for defining said modified tooth geometry.

40. The computerized method according to claim 38, wherein said stripping surface is used to generate said IPR tooth model by at least one of trimming a three-dimensional model of a tooth and by generating a deformed tooth model by adjusting geometry of vertices located on one side of the stripping plane.

41. The computerized method according to claim 38, wherein said constructing a modified tooth geometry comprises providing stage-dependent geometry models for a plurality of stripping stages.

42. A method of digitally representing an interproximal reduction (IPR) tooth model for a plurality of teeth of a patient wherein the digital representation of the IPR for said plurality of teeth are generated using a computing device performing the following process:
   determining whether stripping is needed for a first tooth with a second tooth within said plurality of teeth;
   generating an IPR tooth model for said first tooth based on the potential collision with the second tooth including constructing a stripping surface for the tooth by constructing a stripping plane for the first tooth by determining a normal direction of the stripping plane based on local coordinate systems for the first tooth or other appropriate references and the second tooth, and determining a target point between contours associated with the first tooth and the second tooth, with the stripping plane being constructed to pass through the target point and in the normal direction;
   determining a stripping amount for said first tooth using the IPR tooth model; and
   repeating said process for remainder of said plurality of teeth.

43. The digital representations according to claim 42, wherein said stripping surface is used to construct at least one of one of a trimmed IPR tooth model and a deformed IPR tooth model.

44. The digital representations according to claim 42, wherein said stripping surface comprises a stripping plane constructed by:
   constructing a first plane in a first tooth and a second plane in said second tooth;
   determining an intersection line between said first plane and said second plane;
   constructing a projection plane and find an intersection point based on said intersection line;
   determining contours associated with said first tooth and said second tooth;
   determining tangent lines for said contours passing through said intersection point;
   determining a normal line to define normal direction for said stripping plane;
   determining an intermediate point between endpoints of said contours; and
   constructing said stripping plane in said normal direction and through said intermediate point.

45. A computerized system for interproximal reduction (IPR) tooth modeling of a patient to facilitate orthodontic treatment, said computerized system comprising:
   a microprocessor; and
   a memory device including instructions for a plurality of algorithms;
   wherein the microprocessor is configured for:
   determining whether stripping is needed for a tooth between any neighboring teeth based on a potential for collision with the neighboring teeth;
   generating an interproximal reduction (IPR) tooth model for said tooth based on the potential collision with the neighboring teeth including constructing a stripping surface for the tooth by constructing a stripping plane for the tooth by determining a normal direction of the stripping plane based on local coordinate systems for the tooth or other appropriate references and at least one neighboring tooth, and determining a target point between contours associated with the tooth and the at least one neighboring tooth, with the stripping plane being constructed to pass through the target point and in the normal direction; and
   determining a stripping amount for said tooth using the IPR tooth model.

* * * * *

UNITED STATES PATENT AND TRADEMARK OFFICE
CERTIFICATE OF CORRECTION

PATENT NO. : 7,689,398 B2  Page 1 of 1
APPLICATION NO. : 11/468639
DATED : March 30, 2010
INVENTOR(S) : Jihua Cheng et al.

It is certified that error appears in the above-identified patent and that said Letters Patent is hereby corrected as shown below:

Title Page, Item (74), Attorney, Agent or Firm, delete "O'Neil" and insert -- O'Neill --, therefor.

In column 3, line 59, delete "maimers" and insert -- manners --, therefor.

In column 5, line 42, delete "$W_A \geqq 0, W_B \geqq 0$" and insert -- $W_A \geq 0, W_B \geq 0$ --, therefor.

In column 5, line 59, delete "$Wi \geqq 0$, and $\Sigma Wi=1$" and insert -- $W_i \geq 0, \Sigma W_i=1$ --, therefor.

In column 6, line 47-48, delete "$W_A \geqq 0, W_B \geqq 0$" and insert -- $W_A \geq 0, W_B \geq 0$ --, therefor.

In column 9, line 51, In Claim 7, delete "$W_A > 0, W_B > 0$" and insert -- $W_A \geq 0, W_B \geq 0$ --, therefor.

In column 10, line 5, In Claim 10, delete "$W_A > O, W_B > O$" and insert -- $W_A \geq 0, W_B \geq 0$ --, therefor.

In column 10, line 14, In Claim 11, delete "$W_i->0$," and insert -- $W_i \geq 0$, --, therefor.

In column 10, line 62, In Claim 15, delete "the plane" and insert -- the stripping plane --, therefor.

In column 11, line 26, In Claim 20, after "said" insert -- first --, therefor.

In column 11, line 29, In Claim 20, delete "$W_A > 0, W_B > 0$" and insert -- $W_A \geq 0, W_B \geq 0$ --, therefor.

In column 11, line 50, In Claim 23, delete "$W_A > O, W_B > O$" and insert -- $W_A \geq 0, W_B \geq 0$ --, therefor.

In column 11, line 59, In Claim 24, delete "$W_i->0$," and insert -- $W_i \geq 0$, --, therefor.

In column 13, line 26, In Claim 38, delete "of the" and insert -- of a --, therefor.

Signed and Sealed this

Thirteenth Day of July, 2010

David J. Kappos
*Director of the United States Patent and Trademark Office*